US011266488B2

(12) United States Patent
Deng et al.

(10) Patent No.: US 11,266,488 B2
(45) Date of Patent: Mar. 8, 2022

(54) TISSUE REPAIR FIBER MEMBRANE, PREPARATION METHOD AND APPLICATION THEREOF, AND TISSUE REPAIR PRODUCT

(71) Applicant: Medprin Regenerative Medical Technologies Co., Ltd., Guangzhou (CN)

(72) Inventors: Kunxue Deng, Guangdong (CN); Yuyu Yuan, Guangdong (CN)

(73) Assignee: Medprin Regenerative Medical Technologies Co., Ltd., Guangdong (CN)

( * ) Notice: Subject to any disclaimer, the term of this patent is extended or adjusted under 35 U.S.C. 154(b) by 655 days.

(21) Appl. No.: 15/779,316

(22) PCT Filed: Nov. 25, 2016

(86) PCT No.: PCT/CN2016/107264
§ 371 (c)(1),
(2) Date: May 25, 2018

(87) PCT Pub. No.: WO2017/088818
PCT Pub. Date: Jun. 1, 2017

(65) Prior Publication Data
US 2018/0344632 A1    Dec. 6, 2018

(30) Foreign Application Priority Data

Nov. 27, 2015   (CN) .......................... 201510854225.8

(51) Int. Cl.
*A61L 27/24*   (2006.01)
*A61F 2/00*    (2006.01)
(Continued)

(52) U.S. Cl.
CPC ............ *A61F 2/0063* (2013.01); *A61L 27/24* (2013.01); *A61L 31/041* (2013.01); *A61L 31/044* (2013.01);
(Continued)

(58) Field of Classification Search
CPC ...... A61L 31/04; A61L 31/041; A61L 31/044; A61L 31/046; A61L 31/047; A61F 2/0063; A61F 2/0077; A61F 2002/0086
See application file for complete search history.

(56) References Cited

U.S. PATENT DOCUMENTS

2003/0100944 A1* 5/2003 Laksin .................... A61L 27/18
                                                    623/1.44
2014/0081414 A1* 3/2014 Hall ......................... D01F 6/12
                                                    623/23.7

FOREIGN PATENT DOCUMENTS

CN   102926129 A   2/2013
CN   103800097 A   5/2014
(Continued)

OTHER PUBLICATIONS

Written Opinion of the International Searching Authority, dated Jun. 1, 2017, 5 pages.
(Continued)

*Primary Examiner* — Sarah W Aleman
(74) *Attorney, Agent, or Firm* — Sheppard Mullin Richter & Hampton LLP (57) ABSTRACT

A tissue repair fibrous membrane, preparation method and application thereof, and tissue repair product. The tissue repair fibrous membrane is formed by interweaving fiber filaments having a diameter of 10 nm to 100 μm, and has pore structures formed by interweaving between the fiber
(Continued)

filaments. The fiber filaments have concave structures, and have annular convex structures thereon in the radial direction of the filaments.

10 Claims, 4 Drawing Sheets

(51) Int. Cl.
*A61L 31/04* (2006.01)
*A61L 31/16* (2006.01)
*A61K 9/00* (2006.01)
*A61K 45/06* (2006.01)

(52) U.S. Cl.
CPC ........... *A61L 31/046* (2013.01); *A61L 31/047* (2013.01); *A61F 2/0045* (2013.01); *A61F 2002/0068* (2013.01); *A61F 2002/0086* (2013.01); *A61K 9/0024* (2013.01); *A61K 45/06* (2013.01); *A61L 31/16* (2013.01); *A61L 2300/236* (2013.01); *A61L 2300/252* (2013.01); *A61L 2430/00* (2013.01)

(56) References Cited

FOREIGN PATENT DOCUMENTS

| CN | 103911767 A | 7/2014 |
|----|-------------|--------|
| CN | 104532480   | 4/2015 |

OTHER PUBLICATIONS

European Patent Application EP 2921136A1, Filed Nov. 14, 2013, 45 pages.
Extended European Search Report Application No. 16868041.1-1122/3375461, PCT/CN2016/107264, 7 pages.
CN201510854225 First Office Action dated Jan. 4, 2019, 9 pages.
CN106492272B First Office Action Application No. 201510852445.7, dated Jan. 3, 2019, 9 pages.
Encapsulation of Drug Reservoir in Fibers by Emulsion Electrospinning: Morphology Characterization and Preliminary Release Assessment, Hongxu Qi et al. Revised Manuscript Received Jun. 2, 2006, 4 pages.

* cited by examiner

TISSUE REPAIR FIBER MEMBRANE, PREPARATION METHOD AND APPLICATION THEREOF, AND TISSUE REPAIR PRODUCT

CROSS REFERENCE TO RELATED APPLICATIONS

The present application is the U.S. national stage application of International Application PCT/CN2016/107264, filed Nov. 25, 2016, which claims priority to Chinese Patent Application No. 201510854225.8, filed Nov. 27, 2015, the contents of which are incorporated herein by reference in their entireties in the present disclosure.

TECHNICAL FIELD

This disclosure relates to a fibrous membrane for tissue repair, a preparation method thereof as well as a use thereof, and a product for tissue repair.

BACKGROUND

Repairing a tissue or an organ with a membrane for tissue repair is rather common in modern surgery operation. A membrane for tissue repair may be used to repair, for example, a hernia, pelvic floor dysfunction, dural mater/meningeal defect, nerve conduit injury, blood vessel, ligament, bone defect, or the like. Due to the particularity of human tissue in structure and function, an ideal fibrous membrane for tissue repair needs to: (1) be good in biocompatibility, capable of guiding tissue growth, and obtain ideal repair; (2) help a tissue regenerate itself by facilitating cell adhesion, crawling and growth; (3) be strong enough to resist mechanical stress before a healthy tissue is completely formed, in applications such as repair peritoneum, ligament, achilles tendon, or the like; (4) be so soft as to reduce the patient's discomfort and improve the effect of the surgery; (5) be easily cut and not fall apart in clinic use; (6) maintain good dimensional stability after being implanted in the body, and be easily sutured to or attached to a tissue, without shrinkage, deformation or displacement; (7) prevent bacteria from hiding and growing and avoid infection caused by utilizing artificial biosynthesized material; and (8) more advantageously, be degraded and assimilated in the body after the completion of the repair.

The existing membranes for tissue repair are usually defective in the following aspects:

1) A woven mesh, as the most common one of the prevailing fibrous membranes for tissue repair, is rough on the surface, stiff, undegradable in the body, less biocompatible, and easy to cause pains and a foreign body sensation. It can result in common complications like erosion and infection. It also brings about severe immunological rejection and postoperative problems. When coming into direct contact with an internal organ, it will probably damage the organ or cause severe tissue adhesion, cause severe foreign body and immune response, which requires one more surgical procedure to remove the membrane and thereby would bring about pain to the patient and even threaten his life.

2) An electrospinning membrane made by the conventional process is stiff and lacks structural diversity, so it may not satisfactorily attach to a tissue in clinical use. Besides, its compactness makes it hard for cells to grow inside it or makes cell growth inside it rather slow. Hence, it does not satisfy the requirements for clinical use.

The existing fibrous membranes for tissue repair, formed by a weaving or electrospinning process, are not ideal in performance.

SUMMARY

The technical problem to be solved by this disclosure is to provide a fibrous membrane for tissue repair, which is mechanically strong enough to support the tissue before it is completely repaired, it is biocompatible to facilitate cell adhesion and proliferation and guide cell differentiation, it may closely attach to the tissue, and reduce the occurrence of shrinkage, infection or organ adhesion, it makes the patient feel more comfortable, and alleviates the patient's suffering by speeding up the repair.

This disclosure provides a fibrous membrane for tissue repair that is formed by interweaving fiber filaments of 10 nm-100 µm in diameter. The fibrous membrane is provided with pore structures formed by interweaving between the filaments. The filaments include concave structures, and include annular convex structures thereon in the radial direction of the filaments.

The fibrous membrane for tissue repair according to this disclosure, an interval of 0.1-3 µm exists between adjacent annular convex structures along the length direction of the filaments.

The fibrous membrane for tissue repair according to this disclosure, the pore structures have an average pore size of 0.5-100 µm.

The fibrous membrane for tissue repair according to this disclosure has a porosity of 30-90%.

The fibrous membrane for tissue repair according to this disclosure has a fluffiness of 2-200 cm$^3$/g.

The fibrous membrane for tissue repair according to this disclosure has a tensile strength of 0.5-10 MPa and an elongation at break of 10-500%.

The fibrous membrane for tissue repair according to this disclosure has a thickness of 0.1-1 mm and has a bursting strength of 0.1 kPa or more.

The filament of the fibrous membrane for tissue repair according to this disclosure is made of one or more kinds of material selected from the following: collagen, hydrophilic polyurethane, cellulose, chondroitin sulfate, chitosan, modified chitosan, fibrin, silk protein, elastin mimetic peptide polymer, heparin, agar, dextran, alginic acid, modified cellulose, alginic acid, starch, polyols, block polyethers, gelatin, polyvinylpyrrolidone, hydrophobic polyurethane, polycaprolactone, polyglycolic acid, polylactic acid-glycolic acid copolymer, 1,3-propylene glycol polymer, polylactic acid-caprolactone copolymer, polylactic acid, polyethylene and its derivatives, and polyethylene terephthalate and its derivatives.

The fibrous membrane for tissue repair according to this disclosure, the polyols are polyvinyl alcohols or polyethylene glycols, and the block polyethers are polyoxyethylene-polyoxypropylene-polyoxyethylene triblock copolymers.

The fibrous membrane for tissue repair according to this disclosure is made by additive manufacturing, including one of or a combination of electrospinning, centrifugal spinning, melt spinning, melting electrospinning, and 3D printing.

The fibrous membrane for tissue repair according to this disclosure is made by electrospinning.

The fibrous membrane for tissue repair according to this disclosure is made by fixing its shape at a temperature of 30-60° C. under a vacuum of −0.06 MPa to −0.12 MPa.

This disclosure also provides a method of preparing a fibrous membrane for tissue repair, the method includes a step of electrospinning.

The method according to this disclosure comprising the following steps:

(1) dissolving a filament material in a solvent to obtain a filament solution;

(2) loading an electrospinning syringe with the filament solution obtained in step (1), performing electrospinning such that when arriving at a collector, the filaments contain the solvent not yet evaporated, and forming a fibrous membrane by collecting the filaments as membrane-like structure; and (3) fixing the four sides of the fibrous membrane obtained in step (2), and fixing the shape of the fibrous membrane at a temperature of 30-60° C. under a vacuum of −0.06 MPa to −0.12 MPa, thereby giving a fibrous membrane for tissue repair.

The method according to this disclosure, the filament solution has a concentration of 4-9 g/dL.

The method according to this disclosure, the filament material satisfies a condition that a solution of the filament material in chloroform at a concentration of 0.1 g/dL has a viscosity of 0.5-6.5 dL/g.

The method according to this disclosure, the electrospinning is performed at room temperature and atmosphere pressure.

The method according to this disclosure, the spinning apparatus has an inner temperature of 5-35° C. and a relative humidity of 20-90% when performing electrospinning.

The method according to this disclosure, a micro-syringe pump is adjusted to operate at a rate of 2.5-10 mL/h, a high-voltage generator is adjusted to generate a voltage difference of 5-45 kV, and the collector is adjusted to collect the filament at a distance of 14-30 cm when performing electrospinning.

The method according to this disclosure, in step (3), comprising wetting the fibrous membrane with an ethanol aqueous solution or absolute ethanol before fixing its shape such that the fibrous membrane is not in a complete swelling condition. "A complete swelling condition" means that both the surface and the interior of the filaments are in an evenly swelling condition. "Not in a complete swelling condition" means that not both the surface and the interior of the filaments are in an evenly swelling condition.

The method according to this disclosure, in step (3), when fixing the shape of the fibrous membrane, the temperature is elevated from room temperature to a set temperature at a rate of 0.01-1° C./s. This disclosure further provides use of the fibrous membrane for tissue repair in preparing a product for tissue repair.

This disclosure further provides a product for tissue repair made of the fibrous membrane for tissue repair.

This disclosure is superior to the prior art in that:

(1) The fibrous membrane for tissue repair according to this disclosure is provided with pore structures formed by interweaving between the filaments. The filaments include concave structures, and further include annular convex structures thereon in the radial direction of the filaments. Thus, the fibrous membrane has a greatly increased specific surface area, which facilitates cell adhesion, crawling and growth.

(2) The fibrous membrane for tissue repair according to this disclosure is provided with pore structures formed by interweaving between the filaments. The filaments include concave structures, and further include annular convex structures thereon in the radial direction of the filaments. Thus, the fibrous membrane for tissue repair has an increased bursting strength, an increased adhesion, and an increased specific surface area. The fibrous membrane for tissue repair is capable of being finely attached to the tissue where the fibrous membrane is applied, achieving an ideal bursting strength, and facilitating the repair and regeneration of the tissue itself.

(3) The high porosity of the fibrous membrane for tissue repair according to this disclosure facilitates cell adhesion, crawling and growth and thus makes the tissue regeneration faster.

(4) The fibrous membrane for tissue repair according to this disclosure has a higher water absorbing capacity and is softer. It becomes further softer after being wetted. Thus, the softened fibrous membrane may attach to tissue better in clinical use.

(5) The fibrous membrane for tissue repair according to this disclosure maintains good dimensional stability after being implanted in human body, neither shrinking nor deforming.

(6) The fibrous membrane for tissue repair according to this disclosure feels soft to the touch and may be folded into various shapes, thereby enhances the operability of the surgery and makes the patient less uncomfortable, thus improves the effect of the surgery.

(7) The fibrous membrane for tissue repair according to this disclosure is of good biocompatibility and capable of guiding tissue growth, thereby leading to ideal repair.

(8) The method of preparing the fibrous membrane for tissue repair according to this disclosure is simple and needs a short production time. Thus, it may prevent the product from being polluted during the production, and may help to control the product's quality more readily, thus makes it easy for a product standard to be achieved, thereby makes it possible to produce the product at low costs with high efficiency.

DETAILED DESCRIPTION

The fibrous membrane for tissue repair of this disclosure is formed by interweaving fiber filaments of 10 nm-100 μm in diameter. The fibrous membrane is provided with pore structures formed by interweaving between the filaments. The filaments include concave structures, and include annular convex structures thereon in the radial direction of the filaments.

The annular convex structure refers to a structure formed on the filament that protrudes in the direction perpendicular to the length direction of the filament (i.e., radial direction) and surrounds the filament. The annular convex structure is not a string-of-pearls structure illustrated in, for example, Encapsulation of drug reservoirs in fibers by emulsion electrospinning: Morphology characterization and preliminary release assessment (Qi, et al., Biomacromolecules, 2006, 7(8): 2327-2330). In the string-of-pearls structure, the convex structure of a filament has a diameter far greater than that of the filament itself. The string-of-pearls structure is usually considered as a failed product of electrospinning. The annular convex structures herein are lengthwise spaced by intervals of 0.1-3 μm. The filament with the annular convex structures has a diameter of 10 nm-100 μm, preferably 30 nm-50 μm. The diameter of the filament with the annular convex structures refers to the diameter of the annular convex structure.

Figure 2:
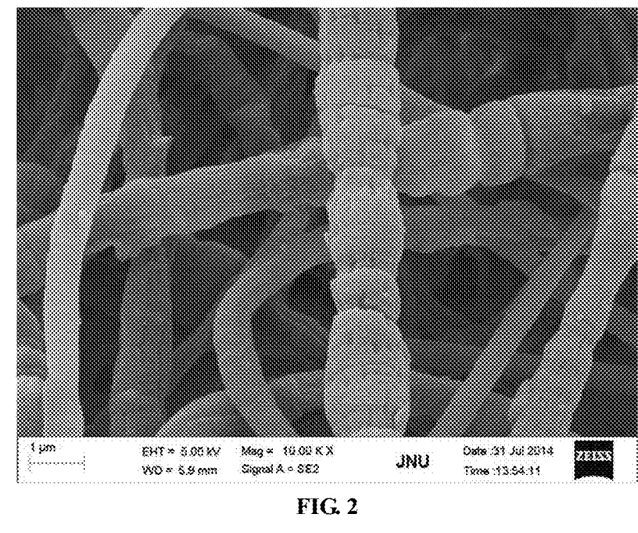
FIG. 2 is an SEM photograph of a section through the fibrous membrane for tissue repair prepared in Example 3, which includes concave structures and annular convex structures.

The fibrous membrane for tissue repair of this disclosure has concave structures including pore structures and pit-like structures and excluding depressions between the annular convex structures (which include, for example, the portion pointed by the arrow in FIG. 2, but are not limited to it—that is, include portions similar to it). The concave structures have an average diameter of 0.005-5 μm, preferable 0.05-3 μm. The average diameter of the concave structures means an average of the longest diameters and the shortest diameters of the pores or pits on the surface of the filaments.

In the fibrous membrane for tissue repair of this disclosure, the filament preferably has a diameter of 0.3-5 μm.

In the fibrous membrane for tissue repair of this disclosure, the pore structures between the filaments have an average diameter of 0.5-100 μm, preferably 1-50 μm.

The fibrous membrane for tissue repair of this disclosure has a porosity of 30-90%, preferably 60-90%.

The fibrous membrane for tissue repair of this disclosure has a fluffiness of 2-200 cm$^3$/g, preferably 4-50 cm$^3$/g.

The fibrous membrane for tissue repair of this disclosure has a tensile strength of 0.5-10 MPa, preferably 1-6 MPa, and has an elongation at break of 10-500%, preferably 20-300%.

The fibrous membrane for tissue repair of this disclosure has a thickness of 0.1-1 mm, preferably 0.2-0.5 mm, and has a bursting strength of 0.1 kPa or more, preferably 0.2 kPa or more.

The fluffiness herein refers to 1000 times of a ratio of the apparent thickness of the fibrous membrane for tissue repair to its area density:

$$\text{Fluffiness} = \text{Apparent thickness } T_0/\text{Area density } \omega \times 10^3.$$

The fluffiness is expressed in unit of cm$^3$/g, the apparent thickness is expressed in unit of mm, and the area density is expressed in unit of g/m$^2$. The apparent thickness $T_0$ is measured by a FAST-1 compressive fabric apparatus in accordance with GB/T 7689.1-2001, and is expressed as a difference between the thickness (mm) of the fibrous membrane for tissue repair at a pressure of 2 cN/cm$^2$ and its thickness (mm) at a pressure of 100 cN/cm$^2$. The area density $\omega$ is the weight per unit area without considering the thickness of the fibrous membrane for tissue repair.

The bursting strength herein was measured by cutting a rabbit's skin into a circle of 3 cm in diameter, and then cutting out a hole having a diameter of 1 cm in the middle; cutting the fibrous membrane for tissue repair of this disclosure into a circle of 3 cm in diameter, wetting the fibrous membrane, and placing it on the rabbit's skin by ensuring that the hole is completely covered; covering the mouth of a container equipped with a pressure sensor with the rabbit's skin to which the fibrous membrane has been attached so as to seal the container; evenly blowing air into the container while recording, as the bursting strength, the value on the sensor when the fibrous membrane is broken.

The porosity herein refers to the percentage of the pores' volume in the bulk volume of the material. It was measured by a gas adsorption method. The pore size distribution was determined by the GB/T mercury porosimetry.

The diameter of the filaments, the diameter of the annular convex structures and the average diameter of the concave structures were determined by SEM. The average diameter of the pore structures between the filaments was determined by the bubble point method using a capillary flow aperture analyzer in accordance with ASTM D 6767-2002. The thickness was determined by a compressive fabric apparatus in accordance with GB/T 7689.1-2001. The tensile strength and elongation at break were determined in accordance with *Determination of Breaking Strength and Elongation at Break of Fabrics* in GB/T 3923.1-1997.

The filament of the fibrous membrane for tissue repair of this disclosure is made of one or more kinds of material selected from the following: collagen, hydrophilic polyurethane, cellulose, chondroitin sulfate, chitosan, modified chitosan, fibrin, silk protein, elastin mimetic peptide polymer, heparin, agar, dextran, alginic acid, modified cellulose, alginic acid, starch, polyols, block polyethers, gelatin, polyvinylpyrrolidone, hydrophobic polyurethane, polycaprolactone (PCL), polyglycolic acid (PGA), polylactic acid-glycolic acid copolymer (PLGA), 1,3-propylene glycol polymer, polylactic acid-caprolactone copolymer (PLC), polylactic acid (PLA), polyethylene and its derivatives, and polyethylene terephthalate and its derivatives. The polyols are polyvinyl alcohols or polyethylene glycols, and the block polyethers are polyoxyethylene-polyoxypropylene-polyoxyethylene triblock copolymers. Preferably, the material of the fibrous filaments is L-polylactic acid (PLGA), polycaprolactone (PCL), polyglycolic acid (PGA), polylactic acid-glycolic acid copolymer (PLGA), polylactic acid-caprolactone copolymer (PLC), polyether F127, gelatin proteins, celluloses, or polyols.

The inventors found that any fibrous membrane allowed water to enter therein if it was put into water and a physical pressure was applied onto it. However, compared with a fibrous membrane without concave structures or annular convex structures on the filaments, the fibrous membrane for tissue repair of this disclosure, at an equal pressure per unit mass in the same conditions, made it easier for water/a solution to enter therein and absorbed more water/solution. Moreover, the fibrous membrane for tissue repair of this disclosure became softer after absorbing water and thus the softened fibrous membrane might attach to a tissue better in clinical use.

The fibrous membrane for tissue repair of this disclosure may be made by additive manufacturing, including one of or a combination of electrospinning, centrifugal spinning, melt spinning, melting electrospinning, and 3D printing. Electrospinning is preferred.

The method of preparing a fibrous membrane for tissue repair according to this disclosure comprising a step of electrospinning.

A preferred method of preparing a fibrous membrane for tissue repair according to this disclosure comprising the following steps:

(1) dissolving a filament material in a solvent to obtain a filament solution;

(2) loading an electrospinning syringe with the filament solution obtained in step (1), performing electrospinning such that when arriving at a collector, the filaments contain the solvent not yet evaporated, and forming a fibrous membrane by collecting the filaments as membrane-like structure; and (3) fixing the four sides of the fibrous membrane obtained in step (2), and fixing the shape of the fibrous membrane at a temperature of 30-60° C. under a vacuum of −0.06 MPa to −0.12 MPa, thereby giving a fibrous membrane for tissue repair.

Preferably, in step (1), the filament solution has a concentration of 4-9 g/dL, more preferably 7.0-7.6 g/dL.

Furthermore, the filament material satisfies the condition that a solution of the filament material in chloroform at a concentration of 0.1 g/dL has viscosity of 0.5-6.5 dL/g, preferably 1.5-4.0 dL/g.

Preferably, in step (2), the electrospinning is performed at room temperature and atmosphere pressure.

Preferably, in step (2), the spinning apparatus has an inner temperature of 5-35° C. and a relative humidity of 20-90% when performing electrospinning. And more preferably, the spinning apparatus has an inner temperature of 10-30° C. and a relative humidity of 30-70%.

In step (2), a micro-syringe pump is preferably adjusted to operate at a rate of 2.5-10 mL/h, more preferably at a rate of 5.0-7 mL/h. A high-voltage generator is preferably adjusted to generate a voltage difference of 5-45 kV, more preferably 18-35 kV. The collector is preferably adjusted to collect the filaments at a distance of 14-30 cm, more preferably 15-28 cm.

In step (3), fixing the shape is performed at 30-60° C., preferably at 35-55° C.

In step (3), comprising wetting the fibrous membrane with an ethanol aqueous solution or absolute ethanol before fixing its shape such that the membrane is not in a complete swelling condition. Preferably, the wetting is performed with an ethanol aqueous solution at a concentration of 50-95 vol % or absolute ethanol for 1 s-1.5 h. More preferably the wetting is performed with an ethanol aqueous solution at a concentration of 75-95 vol % for 1 s-1 h.

Preferably, in step (3), when fixing the shape of the fibrous membrane, the temperature is elevated from room temperature to a set temperature at a constant rate of 0.01-1° C./s, more preferably at a rate of 0.1-0.6° C./s.

Preferably, in step (3), when fixing the shape of the fibrous membrane, the temperature is 30-60° C., preferably at 35-55° C.

In step (3), it is preferable to fix the four sides of the membrane obtained in step (2), and preferably wet it with an ethanol aqueous solution at a concentration of 50-95 vol % or absolute ethanol for 1 s-1.5 h, and fix the shape of the membrane at 35-55° C. by vacuum drying under a vacuum of −0.06 MPa to −0.12 MPa for 24-96 h, preferably 48-72 h, thereby giving a fibrous membrane for tissue repair.

This disclosure further provides use of the fibrous membrane for repair in preparing a product for tissue repair. Preferably, the fibrous membrane for tissue repair of this disclosure is used to prepare a hernia repair patch, a pelvic floor dysfunction repair system (including a pelvic floor repair patch, a urinary incontinence sling, or a fistula repair patch), an artificial rotator cuff, a dura mater repair patch, a meningeal repair patch, artificial skin, a pericardium repair patch, an artificial blood vessel, an artificial nerve conduit, an artificial dental membrane, artificial ligament, artificial achilles tendon, a bone repair product, a wound repair product, a fistula wound repair product, a filling product, and an organ wound repair product.

This disclosure further provides a product for tissue repair made of the fibrous membrane for tissue repair.

The product for tissue repair of this disclosure is preferably a hernia repair patch, a pelvic floor dysfunction repair system (including a pelvic floor repair patch, a urinary incontinence sling, or a fistula repair patch), an artificial rotator cuff, a dura mater repair patch, a meningeal repair patch, artificial skin, a pericardium repair patch, an artificial blood vessel, an artificial nerve conduit, an artificial dental membrane, artificial ligament, artificial achilles tendon, a bone repair product, a wound repair product, a fistula wound repair product, a filling product, or an organ wound repair product.

This disclosure further provides use of the fibrous membrane for tissue repair and the product for tissue repair in repairing a tissue. The fibrous membrane for tissue repair and the product for tissue repair are preferably used in repairing a hernia, pelvic floor dysfunction (including but not limited to a pelvic floor, urinary incontinence, or fistula), rotator cuff, dura mater, meninges, skin, pericardium, blood vessel, nerve conduit, dental membrane, ligament, achilles tendon, and bone (or filling a bone).

This disclosure will be described in more detail by means of Examples. The chemical agents and raw materials used in the Examples are commercially available unless otherwise specified.

EXAMPLES

Example 1

(1) Dissolve PLGA in hexafluoroisopropanol to obtain a PLGA solution (7.4 g/dL). A solution of this PLGA in chloroform at a concentration of 0.1 g/dL has a viscosity of 2.4 dL/g.

(2) Load the syringe connected to the high-voltage spinneret with the PLGA solution obtained in step (1), adjust the collector to be at a distance of 26 cm, adjust the micro-syringe pump to extrude the PLGA solution at a rate of 6 mL/h, adjust the positive voltage to be 25 kV and the negative voltage to be 0 kV, adjust the roller used as the collector to rotate at 100 rpm, perform electrospinning for 6 h, the filaments contained the solvent not yet evaporate when they arrived at the roller, after the completion of the electrospinning, remove the membrane from the roller, and then remove the solvent from the membrane by vacuum drying, thereby obtaining a fibrous membrane with concave structures on the filaments.

(3) Fix the four sides of the fibrous membrane obtained in step (2), and fix the shape of the fibrous membrane by elevating the temperature to 55° C. at a rate of 0.2° C./s and holding the fibrous membrane at 55° C. under a vacuum of −0.1 MPa for 36 h, thereby giving a fibrous membrane for tissue repair. The fibrous membrane for tissue repair includes concave structures and annular convex structures on the filaments.

In this fibrous membrane for tissue repair, the filaments have an average diameter of 1.8±0.1 μm, and the pore structures between the filaments have an average diameter of 2.7±1.3 μm. It has a porosity of 75%, fluffiness of 5 cm$^3$/g, tensile strength of 4.5±1 MPa, elongation at break of 95%, thickness of 0.2±0.02 mm, and bursting strength of 0.22 kPa.

Example 2

(1) Dissolve PLGA in hexafluoroisopropanol to obtain a PLGA solution (7.5 g/dL). A solution of this PLGA in chloroform at a concentration of 0.1 g/dL has a viscosity of 2.3 dL/g.

(2) Load the syringe connected to the high-voltage spinneret with the PLGA solution obtained in step (1), adjust the collector to be at a distance of 27 cm, adjust the micro-syringe pump to extrude the PLGA solution at a rate of 6.2 mL/h, adjust the positive voltage to be 24 kV and the negative voltage to be 0 kV, adjust the roller used as the collector to rotate at 100 rpm, perform electrospinning for 7 h, the filaments contained the solvent not yet evaporated when they arrived at the roller, after the completion of the electrospinning, remove the membrane from the roller, and then remove the solvent from the membrane by vacuum drying, thereby obtaining a fibrous membrane with concave structures on the filaments.

Figure 1:
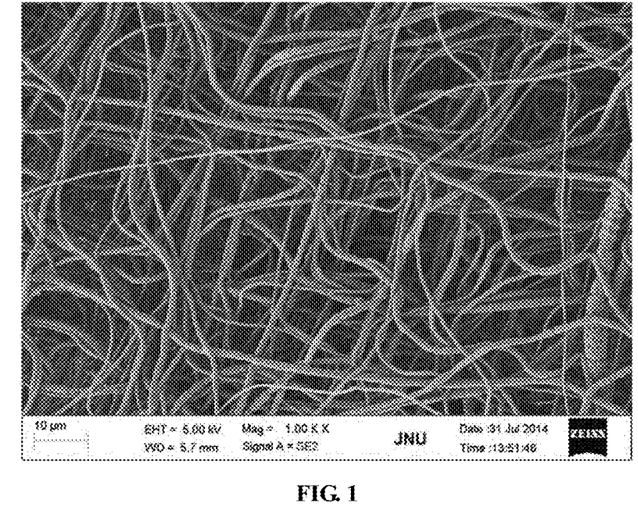
FIG. 1 is a scanning electron microscope (SEM) photograph of a section through the fibrous membrane for tissue repair prepared in Example 2, which includes concave structures and annular convex structures.

(3) Fix the four sides of the fibrous membrane obtained in step (2), wet it with an aqueous ethanol solution at a concentration of 95 vol % for 5 min, and fix the shape of the fibrous membrane by elevating the temperature to 50° C. at a rate of 0.3° C./s and holding the fibrous membrane at 50° C. under a vacuum of −0.098 MPa for 72 h, thereby giving a fibrous membrane for tissue repair. The fibrous membrane for tissue repair includes concave structures and annular convex structures on the filaments. FIG. 1 is an SEM photograph of a section through this fibrous membrane.

In this fibrous membrane for tissue repair, the filaments have an average diameter of 1.9±0.1 μm, and the pore structures between the filaments have an average diameter of 3±1.3 μm. It has a porosity of 80%, fluffiness of 16 cm$^3$/g, tensile strength of 3±0.5 MPa, elongation at break of 30%, thickness of 0.28±0.06 mm, and bursting strength of 0.32 kPa.

Example 3

(1) Dissolve PLGA in hexafluoroisopropanol to obtain a PLGA solution (9.5 g/dL).

(2) Load the syringe connected to the high-voltage spinneret with the PLGA solution obtained in step (1), adjust the collector to be at a distance of 22 cm, adjust the micro-syringe pump to extrude the PLGA solution at a rate of 7 mL/h, adjust the positive voltage to be 24.5 kV and the negative voltage to be 0 kV, adjust the roller used as the collector to rotate at 100 rpm, adjust the spinning apparatus to have an inner temperature of 17° C. and a relative humidity of 90%, perform electrospinning for 4.5 h, the filaments contained the solvent not yet evaporated when they arrived at the roller, after the completion of the electrospinning, remove the membrane from the roller, and then remove the solvent from the membrane by vacuum drying.

(3) Fix the four sides of the membrane obtained in step (2), and fix the shape of the membrane by elevating the temperature to 60° C. at a rate of 0.3° C./s and holding the membrane at 60° C. under a vacuum of −0.11 MPa for 96 h, thereby giving a fibrous membrane for tissue repair. The fibrous membrane for tissue repair includes concave structures and annular convex structures on the filaments. FIG. 2 is an SEM photograph of a section through this fibrous membrane.

In this fibrous membrane for tissue repair, the filaments have an average diameter of 2.0±0.1 μm, and the pore structures between the filaments have an average diameter of 4±2 μm. It has a porosity of 74%, fluffiness of 4 cm$^3$/g, tensile strength of 2.7±0.6 MPa, elongation at break of 90%, thickness of 0.16±0.03 mm, and bursting strength of 0.26 kPa.

Example 4

(1) Dissolve PLGA in hexafluoroisopropanol to obtain a PLGA solution (10 g/dL).

(2) Load the syringe connected to the high-voltage spinneret with the PLGA solution, adjust the collector to be at a distance of 23 cm, adjust the micro-syringe pump to extrude the PLGA solution at a rate of 7.5 mL/h, adjust the positive voltage to be 23.5 kV and the negative voltage to be 0 kV, adjust the roller used as the collector to rotate at 100 rpm, adjust the spinning apparatus to have an inner temperature of 15° C. and a relative humidity of 85%, perform electrospinning for 5.5 h, the filaments contained the solvent not yet evaporated when they arrived at the roller, after the completion of the electrospinning, remove the membrane from the roller, and then remove the solvent from the membrane by vacuum drying.

Figure 3:
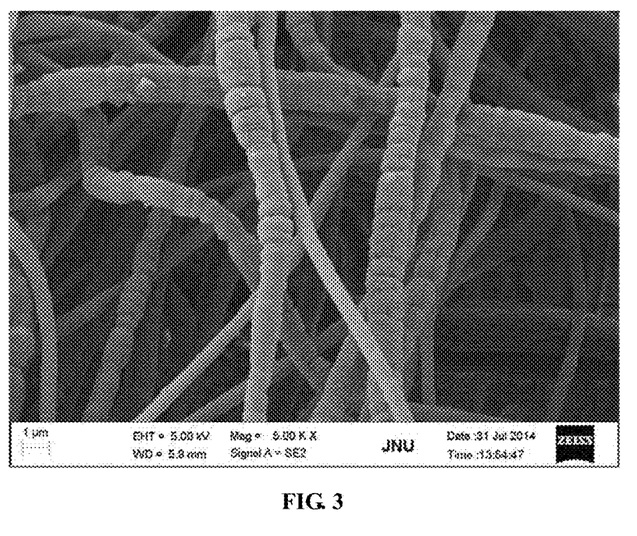
FIG. 3 is an SEM photograph of a section through the fibrous membrane for tissue repair prepared in Example 4, which includes concave structures and annular convex structures.

(3) Fix the four sides of the membrane obtained in step (2), wet it with an aqueous ethanol solution at a concentration of 90 vol % for 5 min, and fix the shape of the membrane by elevating the temperature to 55° C. at a constant rate of 0.2° C./s and holding the fibrous membrane at 55° C. under a vacuum of −0.12 MPa for 48 h, thereby giving a fibrous membrane for tissue repair. The fibrous membrane for tissue repair includes concave structures and annular convex structures on the filaments. FIG. 3 is an SEM photograph of a section through this fibrous membrane.

In this fibrous membrane for tissue repair, the filaments have an average diameter of 2.1±0.1 μm, and the pore structures between the filaments have an average diameter of 5.5±2.5 μm. It has a porosity of 76%, fluffiness of 12 cm$^3$/g, tensile strength of 2.9±0.1 MPa, elongation at break of 110%, thickness of 0.18±0.03 mm, and bursting strength of 0.24 kPa.

Example 5

(1) Dissolve PLGA in hexafluoroisopropanol to obtain a PLGA solution (7.5 g/dL). A solution of this PLGA in chloroform at a concentration of 0.1 g/dL has a viscosity of 2.3 dL/g.

(2) Load the syringe connected to the high-voltage spinneret with the PLGA solution obtained in step (1), adjust the collector to be at a distance of 27 cm, adjust the microsyringe pump to extrude the PLGA solution at a rate of 6.2 mL/h, adjust the positive voltage to be 24 kV and the negative voltage to be 0 kV, adjust the roller used as the collector to rotate at 100 rpm, perform electrospinning for 7 h, the filaments contained the solvent not yet evaporated when they arrived at the roller, after the completion of the electrospinning, remove the membrane from the roller, and then remove the solvent from the membrane by vacuum drying, thereby obtaining a fibrous membrane with concave structures on the filaments.

(3) Fix the four sides of the fibrous membrane obtained in step (2), wet it with an aqueous ethanol solution at a concentration of 85 vol % for 5 min, and fix the shape of the fibrous membrane by elevating the temperature to 55° C. at a constant rate of 0.5° C./s and holding the fibrous membrane at 55° C. under a vacuum of −0.11 MPa for 50 h, thereby giving a fibrous membrane for tissue repair. The fibrous membrane for tissue repair includes concave structures and annular convex structures on the filaments.

In this fibrous membrane for tissue repair, the filaments have an average diameter of 2.1±0.1 μm, and the pore structures between the filaments have an average diameter of 3.9±0.7 μm. It has a porosity of 70%, fluffiness of 14 cm$^3$/g, tensile strength of 3.4±0.5 MPa, elongation at break of 120%, thickness of 0.25±0.06 mm, and bursting strength of 0.28 kPa.

Example 6

(1) Dissolve PLGA in hexafluoroisopropanol to obtain a PLGA solution (4.5 g/dL). A solution of this PLGA in chloroform at a concentration of 0.1 g/dL has a viscosity of 6 dL/g.

(2) Load the syringe connected to the high-voltage spinneret with the PLGA solution obtained in step (1), adjust the collector to be at a distance of 26 cm, adjust the microsyringe pump to extrude the PLGA solution at a rate of 6 mL/h, adjust the positive voltage to be 25 kV and the negative voltage to be 0 kV, adjust the roller used as the collector to rotate at 100 rpm, perform electrospinning for 6 h, the filaments contained the solvent not yet evaporated when they arrived at the roller, after the completion of the electrospinning, remove the membrane from the roller, and then remove the solvent from the membrane by vacuum drying, thereby obtaining a fibrous membrane with concave structures on the filaments.

(3) Fix the four sides of the fibrous membrane obtained in step (2), and fix the shape of the fibrous membrane by elevating the temperature to 45° C. at a rate of 0.1° C./s and holding the fibrous membrane at 45° C. under a vacuum of −0.08 MPa for 36 h, thereby giving a fibrous membrane for tissue repair. The fibrous membrane for tissue repair includes concave structures and annular convex structures on the filaments.

In this fibrous membrane for tissue repair, the filaments have an average diameter of 1.8±0.1 μm, and the pore structures between the filaments have an average diameter of 2.3±1.3 μm. It has a porosity of 70%, fluffiness of 4.5 cm$^3$/g, tensile strength of 4.2±1 MPa, elongation at break of 100%, thickness of 0.2±0.02 mm, and bursting strength of 0.23 kPa.

Example 7

(1) Dissolve PLGA in hexafluoroisopropanol to obtain a PLGA solution (6 g/dL). A solution of this PLGA in chloroform at a concentration of 0.1 g/dL has a viscosity of 1.8 dL/g.

(2) Load the syringe connected to the high-voltage spinneret with the PLGA solution obtained in step (1), adjust the collector to be at a distance of 26 cm, adjust the microsyringe pump to extrude the PLGA solution at a rate of 6 mL/h, adjust the positive voltage to be 25 kV and the negative voltage to be 0 kV, adjust the roller used as the collector to rotate at 100 rpm, perform electrospinning for 7 h, the filaments contained the solvent not yet evaporated when they arrived at the roller, after the completion of the electrospinning, remove the membrane from the roller, and then remove the solvent from the membrane by vacuum drying, thereby obtaining a fibrous membrane with concave structures on the filaments.

(3) Fix the four sides of the fibrous membrane obtained in step (2), and fix the shape of the fibrous membrane by elevating the temperature to 40° C. at a rate of 0.1° C./s and holding the fibrous membrane at 40° C. under a vacuum of −0.07 MPa for 71 h, thereby giving a fibrous membrane for tissue repair. The fibrous membrane for tissue repair includes concave structures and annular convex structures on the filaments.

In this fibrous membrane for tissue repair, the filaments have an average diameter of 1.8±0.1 μm, and the pore structures between the filaments have an average diameter of 2.7±1.2 μm. It has a porosity of 68%, fluffiness of 4.3 cm$^3$/g, tensile strength of 4.3±1 MPa, elongation at break of 106%, thickness of 0.27±0.02 mm, and bursting strength of 0.22 kPa.

Example 8

(1) Dissolve PLGA in hexafluoroisopropanol to obtain a PLGA solution (12 g/dL).

(2) Load the syringe connected to the high-voltage spinneret with the PLGA solution obtained in step (1), adjust the collector to be at a distance of 22 cm, adjust the microsyringe pump to extrude the PLGA solution at a rate of 7 mL/h, adjust the positive voltage to be 24.5 kV and the negative voltage to be 0 kV, adjust the roller used as the collector to rotate at 100 rpm, adjust the spinning apparatus to have an inner temperature of 27° C. and a relative humidity of 30%, perform electrospinning for 4.5 h, the filaments contained the solvent not yet evaporated when they arrived at the roller, after the completion of the electrospinning, remove the membrane from the roller, and then remove the solvent from the membrane by vacuum drying.

(3) Fix the four sides of the fibrous membrane obtained in step (2), and fix the shape of the membrane by elevating the temperature to 35° C. at a rate of 0.3° C./s and holding the membrane at 35° C. under a vacuum of −0.06 MPa for 48 h, thereby giving a fibrous membrane for tissue repair. The fibrous membrane for tissue repair includes concave structures and annular convex structures on the filaments.

In this fibrous membrane for tissue repair, the filaments have an average diameter of 2.3±0.1 μm, and the pore structures between the filaments have an average diameter of 4.2±2 μm. It has a porosity of 76%, fluffiness of 3.8 cm$^3$/g, tensile strength of 3.1±0.6 MPa, elongation at break of 97%, thickness of 0.18±0.03 mm, and bursting strength of 0.21 kPa.

Comparative Example 1

(1) Dissolve PLGA in hexafluoroisopropanol to obtain a PLGA solution (7 g/dL). A solution of this PLGA in chloroform at a concentration of 0.1 g/dL has a viscosity of 2.6 dL/g.

Figure 4:
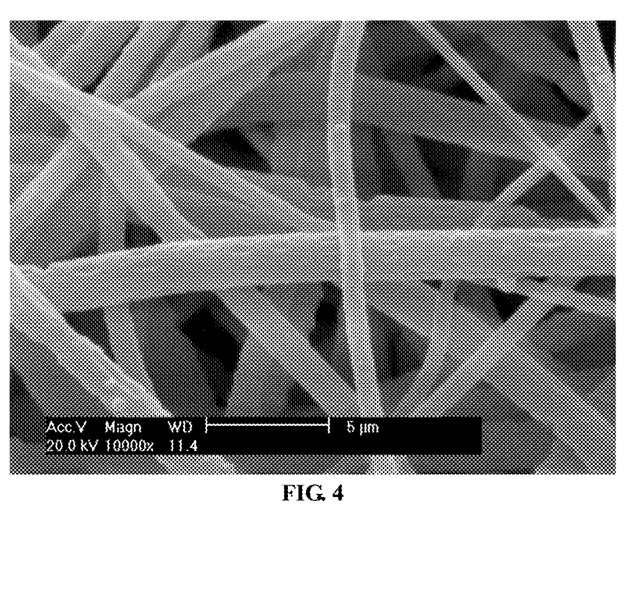
FIG. 4 is an SEM photograph of a section through the fibrous membrane prepared in Comparative Example 1, which includes concave structures.

(2) Load the syringe connected to the high-voltage spinneret with the PLGA solution obtained in step (1), adjust the collector to be at a distance of 22 cm, adjust the microsyringe pump to extrude the PLGA solution at a rate of 5 mL/h, adjust the positive voltage to be 23 kV and the negative voltage to be 0 kV, adjust the roller used as the collector to rotate at 100 rpm, perform electrospinning for 5 h, the filaments contained the solvent not yet evaporated when they arrived at the roller, after the completion of the electrospinning, remove the membrane from the roller, and then remove the solvent from the membrane by vacuum drying, thereby obtaining a fibrous membrane with concave structures on the filaments. FIG. 4 is an SEM photograph of a section through this fibrous membrane.

In this fibrous membrane, the filaments have an average diameter of 1.4±0.1 μm, and the pore structures between the filaments have an average diameter of 2.5±1 μm. It has a porosity of 40%, fluffiness of 2 cm$^3$/g, tensile strength of 3±0.4 MPa, elongation at break of 70%, thickness of 0.2±0.05 mm, and bursting strength of 0.12 kPa.

Comparative Example 2

(1) Dissolve PLGA in hexafluoroisopropanol to obtain a PLGA solution (7.2 g/dL).

(2) Load the syringe connected to the high-voltage spinneret with the PLGA solution obtained in step (1), adjust the collector to be at a distance of 25 cm, adjust the microsyringe pump to extrude the PLGA solution at a rate of 6.3 mL/h, adjust the positive voltage to be 22 kV and the negative voltage to be 0 kV, adjust the roller used as the collector to rotate at 90 rpm, adjust the spinning apparatus to have an inner temperature of 20° C. and a relative humidity of 75%, perform electrospinning for 6 h, the filaments contained the solvent not yet evaporated when they arrived at the roller, after the completion of the electrospinning, remove the membrane from the roller, immerse the membrane in an aqueous ethanol solution to replace residual hexafluoroisopropanol, and then dry the membrane, thereby obtaining a fibrous membrane with concave structures on the filaments.

In this fibrous membrane, the filaments have an average diameter of 1.5±1 μm, and the pore structures between the filaments have an average diameter of 2.4±0.8 μm. It has a porosity of 42%, fluffiness of 2.5 cm$^3$/g, tensile strength of 3.2±0.4 MPa, elongation at break of 90%, thickness of 0.18±0.03 mm, and bursting strength of 0.13 kPa.

Comparative Example 3

(1) Dissolve PLGA in hexafluoroisopropanol to obtain a PLGA solution (10 g/dL).

(2) Load the syringe connected to the high-voltage spinneret with the PLGA solution obtained in step (1), adjust the collector to be at a distance of 23 cm, adjust the microsyringe pump to extrude the PLGA solution at a rate of 7 mL/h, adjust the positive voltage to be 23 kV and the negative voltage to be 0 kV, adjust the roller used as the collector to rotate at 70 rpm, adjust the spinning apparatus to have an inner temperature of 15° C. and a relative humidity of 80%, perform electrospinning for 4 h, the filaments contained the solvent not yet evaporated when they arrived at the roller, after the completion of the electrospinning, remove the membrane from the roller, immerse the membrane in an aqueous ethanol solution to replace residual hexafluoroisopropanol, and then dry the membrane, thereby obtaining a fibrous membrane with concave structures on the filaments.

In this fibrous membrane, the filaments have an average diameter of 1.7±0.1 μm, and the pore structures between the filaments have an average diameter of 2.4±0.6 μm. It has a porosity of 38%, fluffiness of 3 cm$^3$/g, tensile strength of 3±0.5 MPa, elongation at break of 89%, thickness of 0.18±0.3 mm, and bursting strength of 0.15 kPa.

Comparative Example 4

(1) Dissolve PLGA in hexafluoroisopropanol to obtain a PLGA solution (10 g/dL).

(2) Load the syringe connected to the high-voltage spinneret with the PLGA solution obtained in step (1), adjust the collector to be at a distance of 23 cm, adjust the microsyringe pump to extrude the PLGA solution at a rate of 7 mL/h, adjust the positive voltage to be 23 kV and the negative voltage to be 0 kV, adjust the roller used as the collector to rotate at 70 rpm, adjust the spinning apparatus to have an inner temperature of 15° C. and a relative humidity of 80%, perform electrospinning for 4 h, the filaments contained the solvent not yet evaporated when they arrived at the roller, after the completion of the electrospinning, remove the membrane from the roller, immerse the membrane in an aqueous ethanol solution to replace residual hexafluoroisopropanol, and then dry the membrane, thereby obtaining a fibrous membrane with concave structures on the filaments.

In this fibrous membrane, the filaments have an average diameter of 1.8±0.1 μm, and the pore structures between the filaments have an average diameter of 3.5±0.6 μm. It has a porosity of 45%, fluffiness of 5 cm$^3$/g, tensile strength of 3±0.5 MPa, elongation at break of 91%, thickness of 0.18±0.3 mm, and bursting strength of 0.15 kPa.

Comparative Example 5

Prepare a fibrous membrane using the method of Comparative Example 1, except that a PLGA solution at a concentration of 10 g/dL was obtained by dissolving PLGA in hexafluoroisopropanol. The fibrous membrane finally obtained was made of smooth filaments (i.e. the filaments are free from concave structures)—that is, it was an electrospinning fibrous membrane common in the prior art. This fibrous membrane has a porosity of 30% and bursting strength of 0.06 kPa.

Comparative Example 6

Prepare a fibrous membrane using the method of Comparative Example 1, except that a PLGA solution at a concentration of 12 g/dL was obtained by dissolving PLGA in hexafluoroisopropanol. The fibrous membrane finally obtained was made of smooth filaments (i.e. the filaments are free from concave structures). This fibrous membrane has a porosity of 35% and bursting strength of 0.05 kPa.

Comparative Example 7

Prepare a fibrous membrane using the method of Example 1, except that a PLGA solution at a concentration of 11 g/dL was obtained by dissolving PLGA in hexafluoroisopropanol. The fibrous membrane finally obtained was made of filaments having annular convex structures. This fibrous membrane has a porosity of 63% and bursting strength of 0.12 kPa.

Comparative Example 8

Prepare a fibrous membrane using the method of Example 2, except that a PLGA solution at a concentration of 11.5 g/dL was obtained by dissolving PLGA in hexafluoroisopropanol. The fibrous membrane finally obtained was made of filaments having annular convex structures. This fibrous membrane has a porosity of 58% and bursting strength of 0.11 kPa.

To make a convenient comparison, the porosity, fluffiness, tensile strength, elongation at break and bursting strength of the fibrous membranes for tissue repair that were prepared in Examples 1-8 and those of the fibrous membranes that were prepared in Comparative Examples 1-8 are listed in Table 1.

As can be seen from the above, the fibrous membranes for tissue repair of this disclosure, in which the filaments include both concave structures and annular convex structures, have apparently higher porosity and bursting strength, as compared with ordinary electrospinning fibrous membranes. Higher bursting strength enables the fibrous membrane for tissue repair to attach to a tissue in human body stronger, and higher porosity facilitates cell growth. Hence, the fibrous membrane for tissue repair of this disclosure may promote a tissue repair and regenerate itself better.

The inventors compared the fibrous membrane for tissue repair of this disclosure with an ordinary electrospinning membrane in order to verify that the fibrous membrane for tissue repair of this disclosure is superior in water absorption, softness and adhesion to a tissue. Specifically, one piece of the fibrous membrane for tissue repair prepared in Example 1, one piece of the fibrous membrane prepared in Comparative Example 1, and one piece of the fibrous

TABLE 1

Comparison of Performances of Different Fibrous Membranes

| No. | Structure Characteristics of Filaments | Porosity (%) | Fluffiness ($cm^3/g$) | Tensile Strength (MPa) | Elongation at Break (%) | Bursting Strength (kPa) |
|---|---|---|---|---|---|---|
| Example 1 | including concave structures and annular convex structures | 75 | 5 | 4.5 ± 1 | 95 | 0.22 |
| Example 2 | including concave structures and annular convex structures | 80 | 16 | 3 ± 0.5 | 130 | 0.32 |
| Example 3 | including concave structures and annular convex structures | 74 | 4 | 2.7 ± 0.6 | 90 | 0.26 |
| Example 4 | including concave structures and annular convex structures | 76 | 12 | 2.9 ± 0.1 | 110 | 0.24 |
| Example 5 | including concave structures and annular convex structures | 70 | 14 | 3.4 ± 0.5 | 120 | 0.28 |
| Example 6 | including concave structures and annular convex structures | 70 | 4.5 | 4.2 ± 1 | 100 | 0.23 |
| Example 7 | including concave structures and annular convex structures | 68 | 4.3 | 4.3 ± 1 | 106 | 0.22 |
| Example 8 | including concave structures and annular convex structures | 76 | 3.8 | 3.1 ± 0.6 | 97 | 0.21 |
| Comparative Example 1 | including concave structures but without annular convex structures | 40 | 2 | 3 ± 0.4 | 70 | 0.12 |
| Comparative Example 2 | including concave structures but without annular convex structures | 42 | 2.5 | 3.2 ± 0.4 | 90 | 0.13 |
| Comparative Example 3 | including concave structures but without annular convex structures | 38 | 3 | 3 ± 0.5 | 89 | 0.15 |
| Comparative Example 4 | including concave structures but without annular convex structures | 45 | 5 | 3 ± 0.5 | 91 | 0.15 |
| Comparative Example 5 | without concave structures and without annular convex structures | 30 | Not measured | Not measured | Not measured | 0.06 |
| Comparative Example 6 | without concave structures and without annular convex structures | 35 | Not measured | Not measured | Not measured | 0.05 |
| Comparative Example 7 | without concave structures but including annular convex structures | 63 | Not measured | Not measured | Not measured | 0.12 |
| Comparative Example 8 | without concave structures but including annular convex structures | 58 | Not measured | Not measured | Not measured | 0.11 | membrane prepared in Comparative Example 5 were respectively cut into patches of the same size. Each of the patches was put in water and repeatedly pressed by a forefinger pulp to allow water enter therein until it was saturated with water. Then the patches were taken out of the water, and water on their surfaces was removed by gently shaking them a couple of times. The water absorption was determined by a weighting method, and the softness was determined by sensory inspection. The fibrous membrane prepared in Example 1 and that in Comparative Example 5 were respectively attached to a model of brain wrinkles to determine their adhesion to the tissue.

Figure 6:
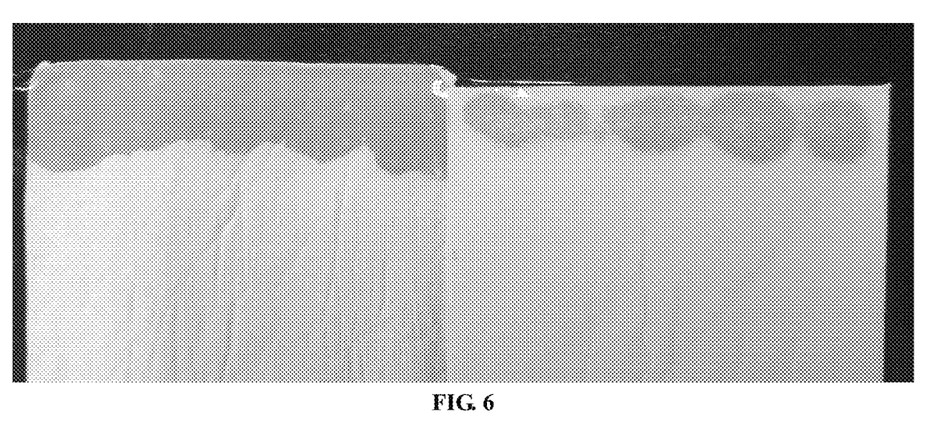
FIG. 6 is a photograph showing the wetting conditions of the fibrous membrane for tissue repair prepared in Example 1 and the fibrous membrane prepared in Comparative Example 5. The left is the fibrous membrane for tissue repair prepared in Example 1 that was pressed in water by a forefinger pulp from one side of the fibrous membrane to the other side for one time. The right is the fibrous membrane prepared in Comparative Example 5 that was pressed in water by a forefinger pulp from one side of the fibrous membrane to the other side for six times.
Figure 7:
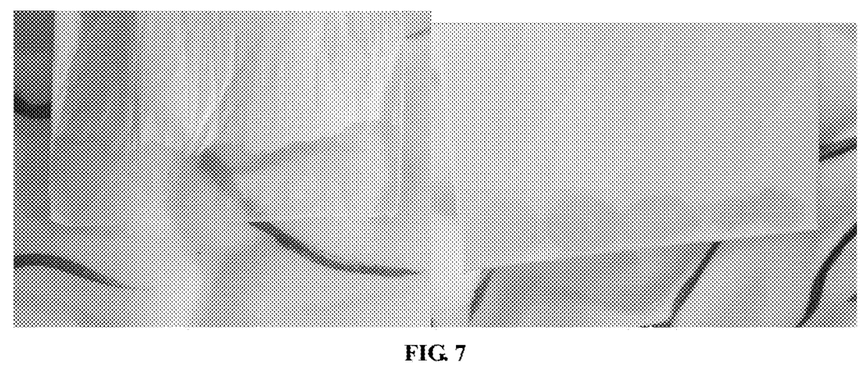
FIG. 7 is a photograph showing how well the fibrous membrane for tissue repair prepared in Example 1 in FIG. 6 after being partially wetted (left) and the fibrous membrane prepared in Comparative Example 5 in FIG. 6 after being partially wetted (right) attach to a model of brain wrinkles.
Figure 8:
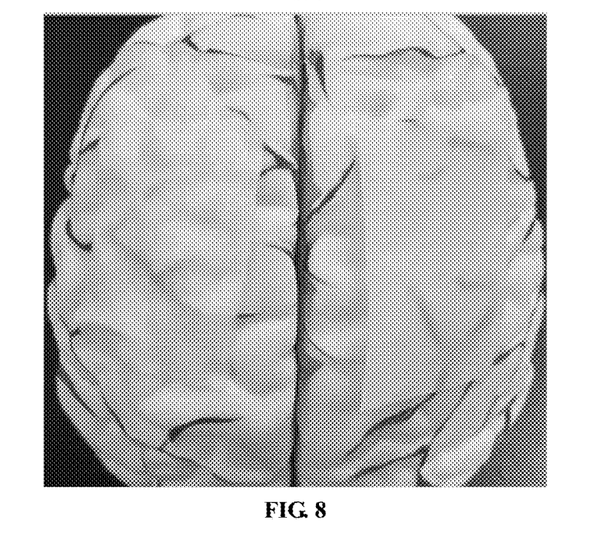
FIG. 8 is a photograph showing how well the fibrous membrane for tissue repair prepared in Example 1 in FIG. 6 after being completely wetted (left) and the fibrous membrane prepared in Comparative Example 5 in FIG. 6 after being completely wetted (right) attach to a model of brain wrinkles.

It was found that at an equal pressure per unit mass, the membrane of Example 1 had a water absorption of 19.6 g/g, the membrane of Comparative Example 1 had a water absorption of 7.1 g/g, and the membrane of Comparative Example 5 had a water absorption of 3.5 g/g. Besides, as shown in FIGS. 6-8, the membrane of Example 1 became wetted more easily under pressure, felt softer, and was completely attached to the model of brain wrinkles after being wetted, whereas the membrane of Comparative Example 5 became wetted after being repeatedly pressed, felt stiff, and may not be attached to the model of brain wrinkles.

The fibrous membranes for tissue repair prepared in Examples 2-8 were also subjected to the above determination, and found to be also excellent in water absorption, softness and adhesion to the tissue. It is proved that the fibrous membrane for tissue repair of this disclosure is superior to the ordinary ones in water absorption, softness and adhesion to tissues.

Use of the Fibrous Membrane for Tissue Repair in Repairing the Dura Mater

The animal test is carried out with dogs, and the fibrous membrane for tissue repair prepared in Example 1 is used in repairing the dura mater defect.

Animal test: general anesthesia was administered to six common domestic dogs (weighting 15-20 kg, 1.5-2 years old) by intramuscular injection of ketamine. The dogs were placed on the operating table after having their heads shaved, and the hair-removal areas were disinfected with 2% iodine and 75% alcohol. The skin and subcutaneous muscles at the middle of the animal's head were longitudinally cut to expose the skull. The periosteum was peeled with a dissector, and the single top cranial plate was exposed. The skull was opened with a high-speed drill to form a bone window at single top. An oval-shaped piece of the dura mater at single top with a size of 3 cm×3 cm was scissored off to make dural mater defect. The fibrous membrane for tissue repair was cut into patches of the appropriate shape and size. Any three of the dogs were selected for their dural mater defects to be repaired by sewing in the patches (suture group), and the other three's dural mater defect was repaired by wetting the patches and directly attaching them to the brain (non-suture group). The muscle and scalp were sutured with 4-0 silk.

Observation of the Suture Group:

The animals were subjected to routine postoperative care and observation. The animals recovered well, the surgical sites healed well, no cerebrospinal fluid leaked, and no epilepsy occurred. Their food intake and water intake were normal, and their outdoor activities were normal as well— that is, no movement disorder was found. They survived till the observation period.

Eighteen months after the surgery, each of the animals' surgical sites together with an area of one centimeter greater than the surgical site, including the artificial dura mater, the peripheral dura mater, and the subdural brain tissue, was cut. The observation of the cut part found that the junction between the fibrous membrane and the dura mater was flat, seamless, without boundary, and completely enclosed, and there was no thickening of the dura mater or part of the dura mater wrapped by the fibrous membrane.

Observation of the Non-Suture Group:

The animals were subjected to routine postoperative care and observation. The animals recovered well, the surgical sites healed well, no cerebrospinal fluid leaked, and no epilepsy occurred. Their food intake and water intake were normal, and their outdoor activities were normal as well— that is, no movement disorder was found. They survived till the observation period.

Figure 5:
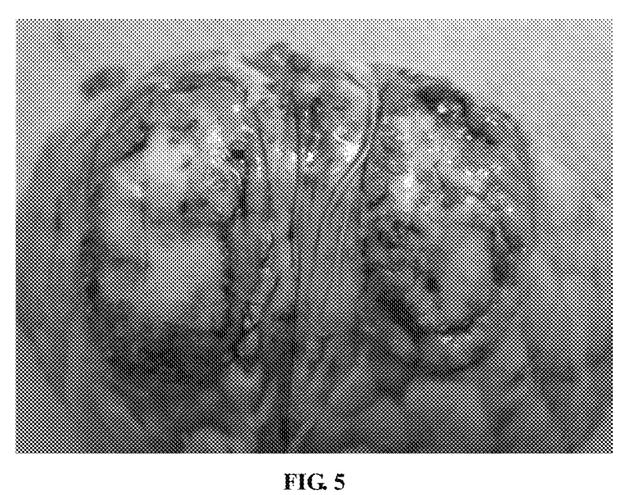
FIG. 5 is a photograph showing the effect of the fibrous membrane for tissue repair prepared in Example 1 after being implanted for 18 months to repair a dura mater.

Eighteen months after the surgery, each of the animals' surgical sites together with an area of one centimeter greater than the surgical site, including the artificial dura mater, the peripheral dura mater, and the subdural brain tissue, was cut. As illustrated in FIG. 5, the junction between the fibrous membrane and the dura mater was flat, seamless, without boundary, and completely enclosed, and there was no thickening of the dura mater or part of the dura mater wrapped by the fibrous membrane.

Good results were also observed when the fibrous membranes for tissue repair prepared in Examples 2-8 were tested by the same animal test. A conclusion may thus be drawn that the fibrous membrane for tissue repair of this disclosure is good in biocompatibility and capable of guiding tissue growth, and may bring about ideal repair results.

INDUSTRIAL APPLICABILITY

The fibrous membrane for tissue repair provided by the Examples of this disclosure is applicable to medical equipment, and is especially usable in manufacturing a product for tissue repair, including a hernia repair patch, a pelvic floor dysfunction repair system, an artificial rotator cuff, a dura mater repair patch, a meningeal repair patch, artificial skin, a pericardium repair patch, an artificial blood vessel, an artificial nerve conduit, an artificial dental membrane, artificial ligament, artificial achilles tendon, a bone repair product, a wound repair product, a fistula wound repair product, a filling product, and an organ wound repair product.

There is a description of the Examples of this disclosure hereinbefore. This disclosure is not limited to those Examples. Changes or substitutes that those skilled in the art can easily think of without departing from the scope disclosed by this disclosure are all covered by the protection scope of this disclosure. The protection scope of this disclosure is subject to the claims.

The invention claimed is:

1. A fibrous membrane for tissue repair, comprising interwoven fiber filaments with pore structures between the filaments, wherein the filaments include pits on the surface of the filaments, and include annular convex structures in the radial direction of the filaments, wherein the annular convex structures have an average diameter of 0.3 to 5 μm and wherein the fibrous membrane has a thickness of 0.1-1 mm and has a bursting strength of 0.1 kPa or more.

2. The fibrous membrane for tissue repair according to claim 1, wherein the adjacent annular convex structures along the length direction of the filaments have an average interval of 0.1-3 μm therebetween.

3. The fibrous membrane for tissue repair according to claim 1, wherein the pore structures have an average pore size of 0.5-100 μm.

4. The fibrous membrane for tissue repair according to claim 1, wherein the fibrous membrane has a porosity of 30-90%.

5. The fibrous membrane for tissue repair according to claim 1, wherein the fibrous membrane has a fluffiness of 2-200 cm$^3$/g.

6. The fibrous membrane for tissue repair according to claim 1, wherein the fibrous membrane has a tensile strength of 0.5-10 MPa and an elongation at break of 10-500%.

7. The fibrous membrane for tissue repair according to claim 1, wherein the filament is made of one or more kinds of material selected from the group consisting of collagen, hydrophilic polyurethane, cellulose, chondroitin sulfate, chitosan, modified chitosan, fibrin, silk protein, elastin mimetic peptide polymer, heparin, agar, dextran, alginic acid, modified cellulose, alginic acid, starch, polyols, block polyethers, gelatin, polyvinylpyrrolidone, hydrophobic polyurethane, polycaprolactone, polyglycolic acid, polylactic acid-glycolic acid copolymer, 1,3-propylene glycol polymer, polylactic acid-caprolactone copolymer, polylactic acid, polyethylene and its derivatives thereof, and polyethylene terephthalate and derivatives thereof.

8. The fibrous membrane for tissue repair according to claim 7, wherein the filament is made of one or more kinds of material selected from the group consisting of polyvinyl alcohols, polyethylene glycols, and polyoxyethylene-polyoxypropylene-polyoxyethylene triblock copolymers.

9. The fibrous membrane for tissue repair according to claim 1, wherein the fibrous membrane is made by a method selected from the group consisting of electrospinning, centrifugal spinning, melt spinning, melting electrospinning, and 3D printing.

10. A product for tissue repair made of the fibrous membrane for tissue repair according to claim 1.

* * * * *